United States Patent
Hopkins et al.

(10) Patent No.: US 6,866,646 B2
(45) Date of Patent: Mar. 15, 2005

(54) SUPINATION/PRONATION THERAPY DEVICE

(75) Inventors: Ronald B. Hopkins, Virginia Beach, VA (US); Richard T. Sieller, Virginia Beach, VA (US)

(73) Assignee: R & R Holdings, LLC, Virginia Beach, VA (US)

(*) Notice: Subject to any disclaimer, the term of this patent is extended or adjusted under 35 U.S.C. 154(b) by 293 days.

(21) Appl. No.: 10/029,852

(22) Filed: Dec. 31, 2001

(65) Prior Publication Data

US 2003/0125651 A1 Jul. 3, 2003

(51) Int. Cl.[7] .................................................. A61F 5/00
(52) U.S. Cl. .............................. 602/5; 602/16; 602/20
(58) Field of Search ............................. 602/20, 5, 16, 602/21, 23–27, 36, 38, 60–64; 601/23, 33, 34, 40, 5, 27, 32, 44; 482/124, 130, 139, 44–46, 112, 118; 128/869, 871, 877–879, 881

(56) References Cited

U.S. PATENT DOCUMENTS

| | | |
|---|---|---|
| 4,100,918 A | 7/1978 | Glancy |
| 4,191,373 A | 3/1980 | Lancellotti |
| 4,408,600 A | 10/1983 | Davis |
| 4,559,932 A * | 12/1985 | Salort ........................ 602/20 |
| 4,763,901 A | 8/1988 | Richter |
| 4,805,606 A | 2/1989 | McDavid, III |
| 4,838,251 A | 6/1989 | Chignon et al. |
| 4,862,878 A | 9/1989 | Davison et al. |
| 5,117,814 A | 6/1992 | Luttrell et al. |
| 5,167,612 A | 12/1992 | Bonutti |
| 5,213,094 A | 5/1993 | Bonutti |
| 5,337,737 A | 8/1994 | Rubin et al. |
| 5,352,190 A | 10/1994 | Fischer et al. |
| 5,365,947 A | 11/1994 | Bonutti |
| 5,383,845 A | 1/1995 | Nebolon |
| 5,437,611 A | 8/1995 | Stern |
| 5,503,619 A | 4/1996 | Bonutti |
| 5,611,764 A | 3/1997 | Bonutti et al. |
| 5,683,336 A | 11/1997 | Pape |
| 5,683,353 A * | 11/1997 | Hamersly .................... 602/16 |
| 5,685,830 A | 11/1997 | Bonutti |
| 5,865,714 A | 2/1999 | Marlowe |
| 5,891,079 A | 4/1999 | Barnes |
| 6,063,048 A | 5/2000 | Bodenschatz et al. |
| 6,113,562 A | 9/2000 | Bonutti et al. |
| 6,117,097 A | 9/2000 | Ruiz |
| 6,179,799 B1 * | 1/2001 | Doran ........................ 602/20 |
| 6,537,237 B1 * | 3/2003 | Hopkins et al. .............. 602/5 |
| 2003/0065281 A1 * | 4/2003 | Hopkins et al. .............. 602/5 |
| 2003/0144620 A1 * | 7/2003 | Sieller et al. ................. 602/5 |

* cited by examiner

Primary Examiner—Henry Bennett
Assistant Examiner—Kathryn Odland
(74) Attorney, Agent, or Firm—John H. Thomas, P.C.

(57) ABSTRACT

An orthotic device promotes both supination and pronation of a patient's wrist. A forearm enclosure is adapted to substantially wrap around a forearm. A forearm support member is adapted to slidably receive the forearm enclosure wherein the support member wraps partially around the forearm enclosure. A post is mountable on the forearm enclosure. An anchor is mounted on the support member. A tensioning member is connected to the anchor and on the other end to the post, wherein a rotational force of supination or pronation will be created on the forearm enclosure depending on the direction which the tensioning members extend from the anchor to the post.

11 Claims, 7 Drawing Sheets

SUPINATION/PRONATION THERAPY DEVICE

The present invention relates to an orthotic device that promotes supination and pronation of a patient's wrist. A combination of components of the device allows it to apply either dynamic or static rotational forces to a joint in need of therapy. The force generated by the components and their direction can be quantified and used in therapeutic treatment.

BACKGROUND OF THE INVENTION

There are many known orthotic devices including those specifically directed to rehabilitation of various joints such as elbows and wrists. Typically, these apparatuses are static or have a single pressure/force that is applied during operation. Those forces may be uneven across the device.

Another problem with existing devices is that none promote rotation or create rotational forces. It is common in wrist or arm injuries to have some temporary or permanent lose of rotation in the forearm/wrist, for instance when an arm is immobilized in a cast for an extended period of time. Whether there is a reduction in the range of supination or pronation, a patient can lose that flexibility of rotation. There are few known therapies to treat this loss of rotation. Typically, any rotational therapy is effectively limited to a therapist's office or similar rehabilitation facility.

SUMMARY OF THE INVENTION

Accordingly, it an object of the present invention to overcome the forgoing drawbacks and problems. The present invention provides a device that creates rotational forces to promote both supination or pronation of a wrist in need of therapy. The forces generated by the device are either dynamic or static. Preferably, the forces can be quantified and used in therapeutic treatment in accordance with treatment guidelines.

In one embodiment, an orthotic device for promoting supination and pronation includes a forearm enclosure adapted to substantially wrap around a forearm. A forearm support member is adapted to slidably receive the forearm enclosure wherein the support member wraps partially around the forearm enclosure. A post is mounted on the forearm enclosure. An anchor is mounted on the support member. A tensioning member is connected on one end to the anchor and on the other end to the post, wherein a rotational force of supination or pronation will be created on the forearm enclosure depending on the direction which the tensioning member is extended from the anchor to the post. The orthotic device may include a plurality of posts mounted at different locations on the forearm enclosure. The tensioning member may be comprised of an elastic material or inelastic material and may have an adjustable length. The orthotic device may further include an upper arm support member connected on one end to the forearm support member and adapted to substantially wrap around and support an upper arm. The upper arm support member may be hindgedly connected or fixedly connected to the forearm support member. The fixed connection from a forearm support member to a upper arm support member may be predetermined, and the predetermined angle may be substantially 90 degrees. The angle of connection of the upper arm support member and forearm support member may be variable.

In another embodiment, an orthotic device for promoting supination and pronation includes a forearm enclosure adapted to substantially wrap around a forearm. A forearm support member is adapted to slidably receive the forearm enclosure wherein the support member wraps partially around the forearm enclosure. Tensioning means have a first end and a second end. The orthotic device further includes means for attaching the tensioning means on the first end to the forearm enclosure and on the second end to the forearm support member. A rotational force of supination or pronation will be created on the forearm enclosure depending on the direction which the tensioning means is attached to the forearm support member and the forearm enclosure.

In a still further embodiment, a kit for assembling an orthotic device includes a forearm enclosure adapted to substantially wrap around a forearm. The kit further includes a forearm support member adapted to slidably receive the forearm enclosure wherein the support member is adapted to wrap partially around the forearm enclosure. A post is mountable on the forearm enclosure. An anchor is mountable on the support member. And the kit further includes a tensioning member connectable on one end to the anchor and on the other end to the post.

DETAILED DESCRIPTION OF PREFERRED EMBODIMENTS

The present invention is directed to an orthotic device used to promote the rotation of a patient's wrist and forearm. The rotation of the wrist in the direction in which the palm is pointed upwardly or skywardly is called supination. The rotation of the wrist in which the palm is facing downwardly is referred to as pronation. The orthotic device described herein can apply either a dynamic or static force in the rotational direction of supination or pronation. Further, that rotational force may be varied by a user or therapist in accordance with the needs of a patient.

Figure 1:
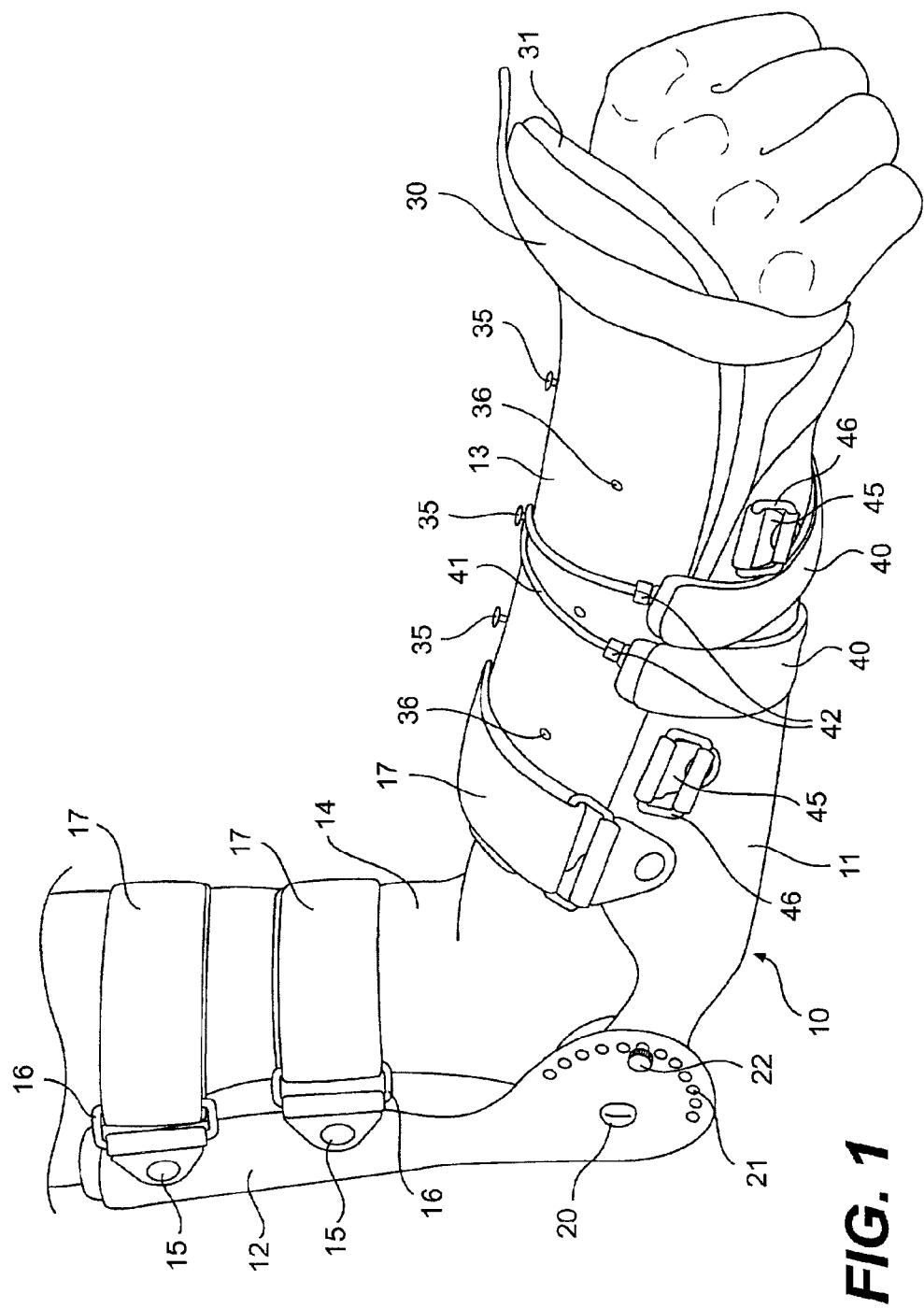
FIG. 1 is a perspective view of an orthotic device in accordance with the present invention.
Figure 2:
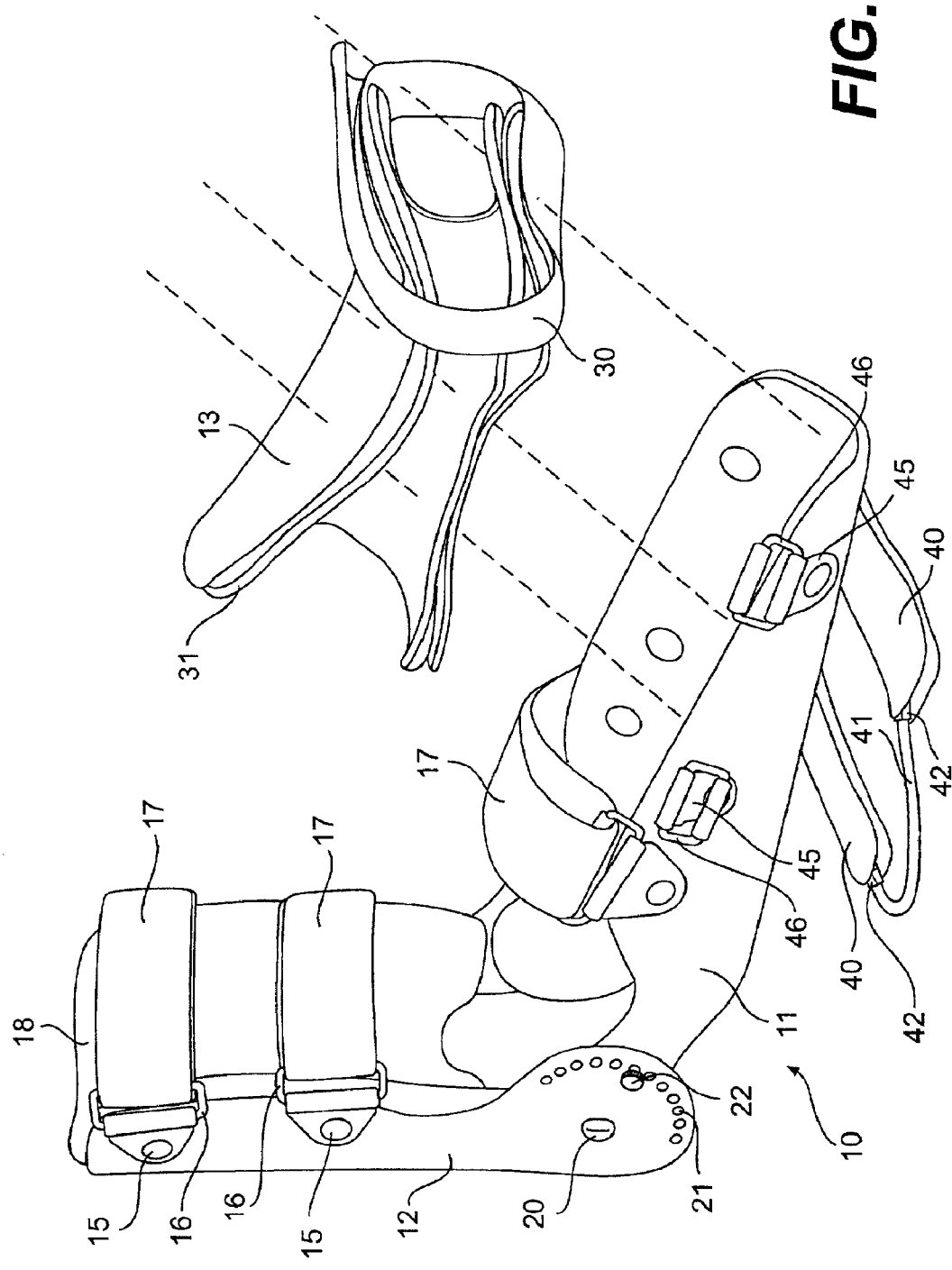
FIG. 2 is a partial, exploded perspective view of the orthotic device shown in FIG. 1.
Figure 4:
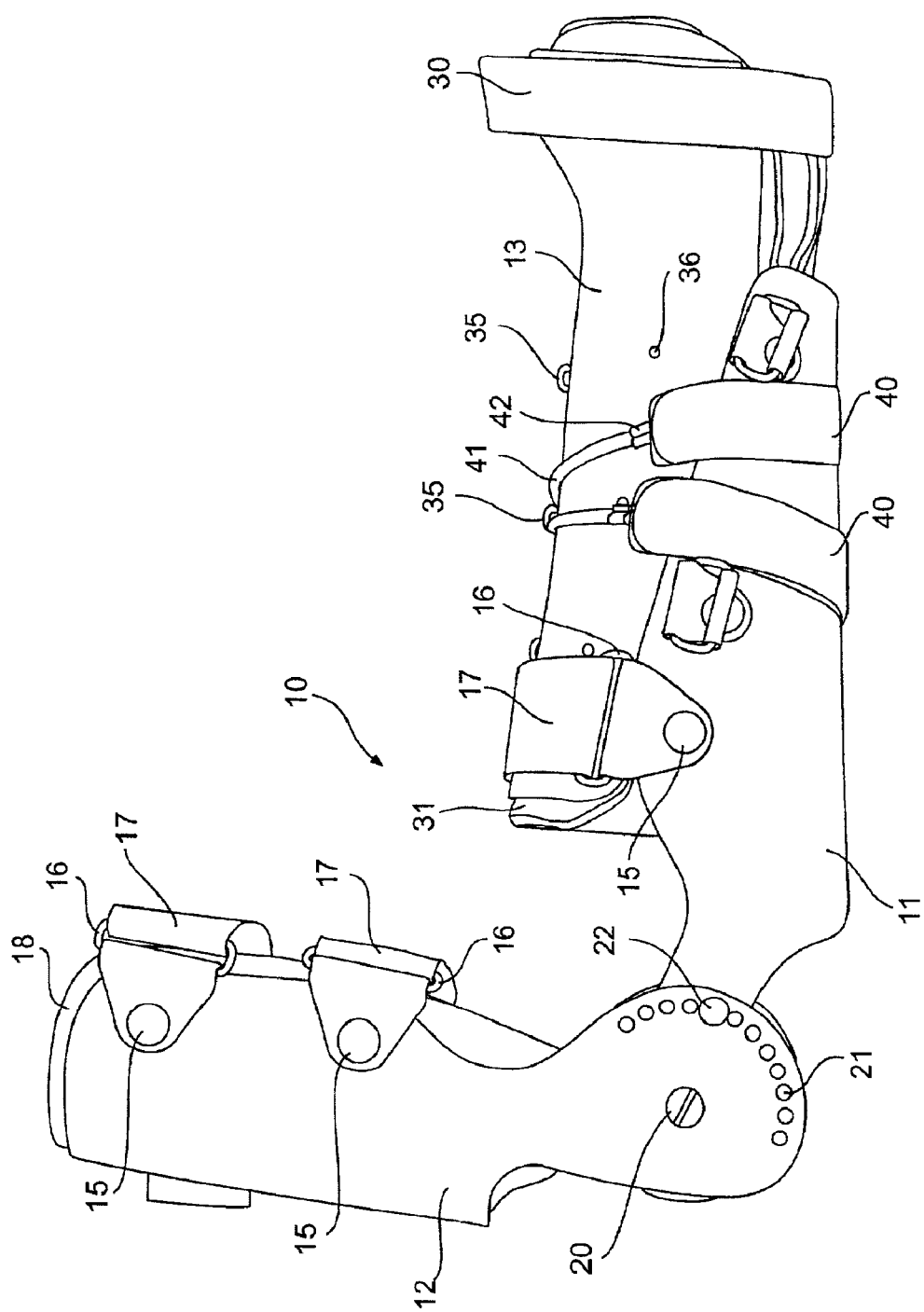
FIG. 4 is a side elevation view of an orthotic device as shown in FIG. 1.

Turning now to the drawings, FIGS. 1,2 and 4 illustrate an orthotic device in accordance with the present invention in which a dynamic force of rotation can be applied to a patient's forearm. (There is reference made throughout of a patient's "wrist" or "forearm" when referring to the application of therapy herein. The terms are effectively referenced to interchangeably.) The orthotic device 10 is a brace adapted to support a patient's upper arm and forearm. The device 10 is made up of a forearm support member 11 and an upper arm support member 12 that are hingedly connected about a hinge 20. A forearm enclosure 13 is adapted to receive and substantially wrap around a patient's forearm. The forearm enclosure 13 is slidably received within the forearm support member 11.

The upper arm support member 12 has two straps 17 that connect the sides of the support member about a patient's arm 14. The straps 17 are made of strips of hook and loop fasteners (VELCRO straps) that loop through rings 16 that are connected by screws 15 to the upper arm support member 12. In this way, the particular size of a patient's arm 14 and the tightness of fit can be accommodated by varying the length of the strap 17.

The hinge 20 attaches the lower end of the upper arm support member 12 to the upper end of the forearm support member 11. The hinge 20 is locked in the substantially 90° relative position (forearm support member to upper arm support member) by a pin 22 releaseably screwed into one of a number of apertures 21. As can be seen, there are a number of apertures 21 thereby allowing the device 10 to have a variable angle defined by the forearm support member 11 and upper arm support member 12. A therapist or patient can predetermine the specific angle that is desirable for a given patient. Of course, the device 10 could have a predetermined, single angle that is nonadjustable. A problem is that many times patients in need of rotational wrist therapy will have other arm injuries that limit the flexion and extension of a patient's arm. Sometimes it is not possible or desirable to have the 90° angle. From a simple supination/pronation therapy standpoint, it is preferred to have the angle of the upper arm relative to the forearm at substantially 90°. In this way, the supination/pronation rotation will be focused on the bones, tendons and muscles in the forearm (wrist) rather than in potential compensating motion of other parts of a patient's arm.

The forearm support member 11 is adapted to receive a forearm enclosure 13 that is wrapped around a forearm. The support member 11 includes a strap 17 that extends from one side of the support member to the other in order to retain the support member attached to a patient's forearm. This strap 17 on the forearm support member 11 is not necessary, but it helps to stabilize the complete device 11. The forearm support member 11 also has rings 46 and screws 45 fastened on either side of the support member. These rings 46 and screws 45 are anchors onto which may be attached straps 40. The straps 40 are part of a tensioning member that includes elastic band 41 that is attached to those straps by clamps 42.

The forearm enclosure 13 is adapted to encircle most of a patient's forearm. The forearm enclosure 13 is preferably molded or fitted to create a snug fit on the forearm. A typical forearm enclosure could be some kind of cast. Other enclosure devices are possible. It is the forearm enclosure 13 that is rotated by the present device, so it must fit tightly enough about the forearm (wrist) to cause the rotation that promotes supination and pronation. In order to make the forearm enclosure 13 fit more comfortably and snugly about a wrist, padding 31 is used to line the inside of the forearm enclosure. The forearm enclosure 13 also includes holes 36. Mounted in the holes 36 are posts 35. The posts 35 are adapted to protrude a small distance from the forearm enclosure 13 yet be securely fitted to it. The forearm enclosure 13 is preferably made of a relatively stiff material. For instance, when a forearm enclosure is a cast, acceptable cast materials include, preferably, Kydex. This can be the same plastic material as the material that makes up the forearm support member 11 and the upper support arm member 12. The forearm enclosure and support member may be fabricated from virtually any material that meets the functional requirements described herein. The plastic material is preferred for its light weight and inexpensive cost. It is essential that the forearm enclosure 13 be able to slide easily over the surface of the inside of the forearm support member 11. This allows for the rotation of the forearm enclosure 13 with minimal drag.

Figure 7A:
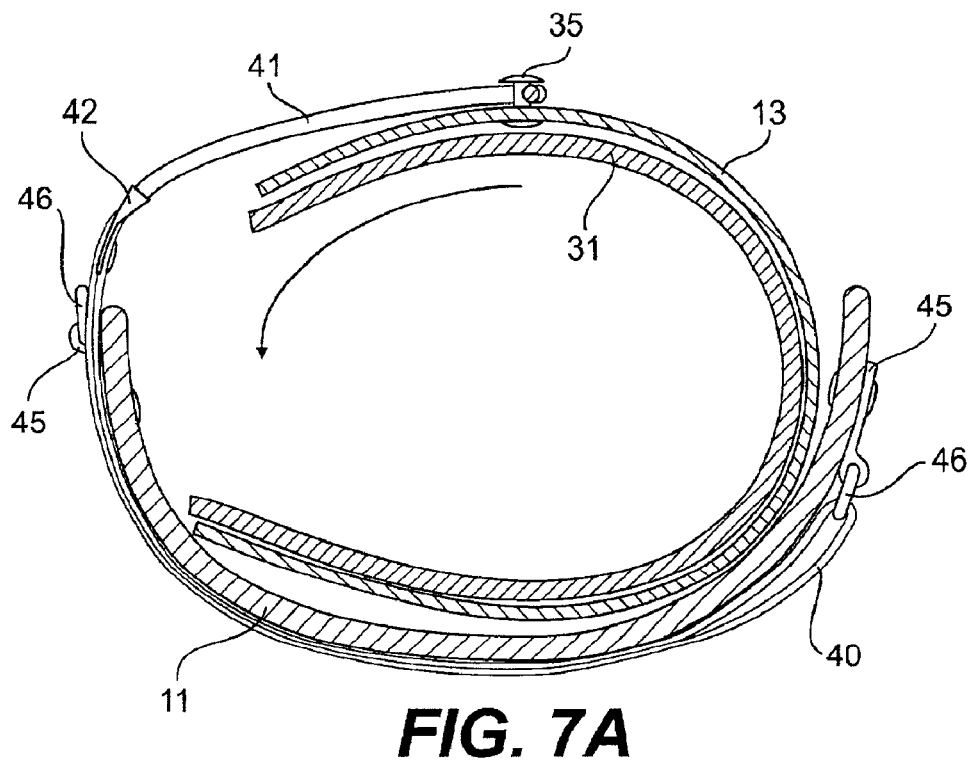
FIGS. 7A and 7B are front elevation, cross-sectional views of a portion of the orthotic device in accordance with the present invention wherein the tensioning member is shown applying a rotational force in the counter clockwise direction(FIG. 7A) and clockwise direction (FIG. 7B).
Figure 7B:
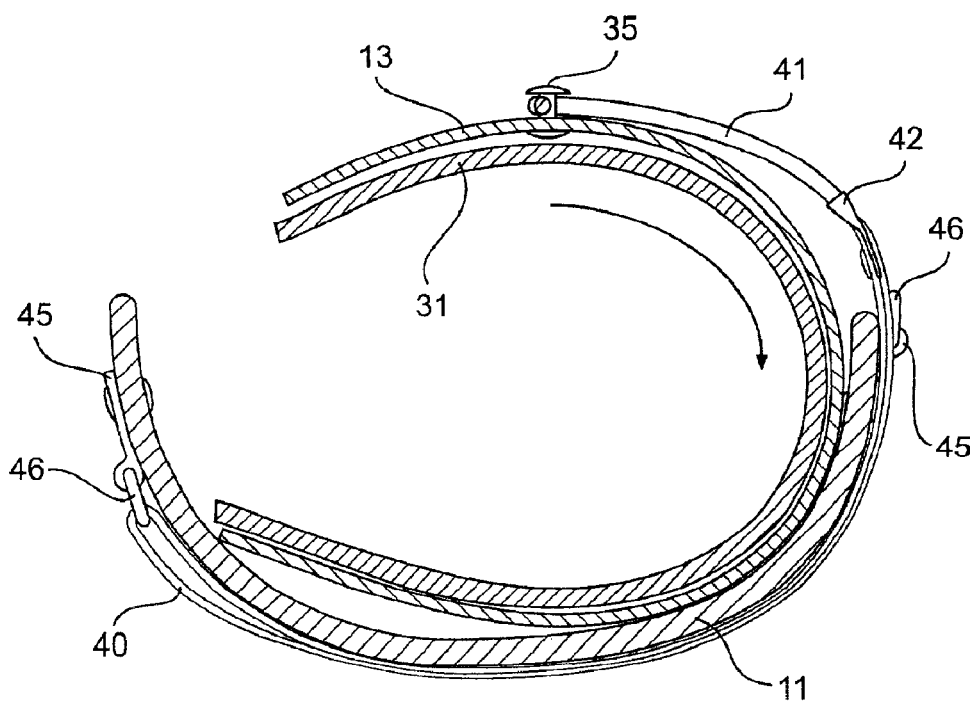

In operation, straps 40 are looped through rings 46 that are in the forearm support member. The straps are then wrapped in a clockwise or counter clockwise direction around the forearm support member 11, and the elastic band 41 is looped over one or more of the posts 35. This creates a dynamic force of rotation in the given direction. By looping the elastic band 41 over more than one post 35, a greater rotational force is created. Also, as can be seen, the posts 35 can be moved to other holes 36 to thereby lessen or increase the amount of rotation and rotational force applied to the forearm inside the forearm enclosure 13. The rotation of the forearm enclosure 13 in the clockwise or counter clockwise direction is best seen in FIGS. 7A and 7B.

In the figures shown, the anchors that are made up of the rings 46 and the bolts 45 are positioned on both sides of forearm support member 11. It is possible to mount any type of anchor in one place, for instance on the bottom of the forearm support member 11, that allows the straps to be easily wrapped in the clockwise or counter clockwise direction. The side mounting of the anchors is a matter of choice to make the bottom of the forearm support member 11 relatively flat.

Figure 3:
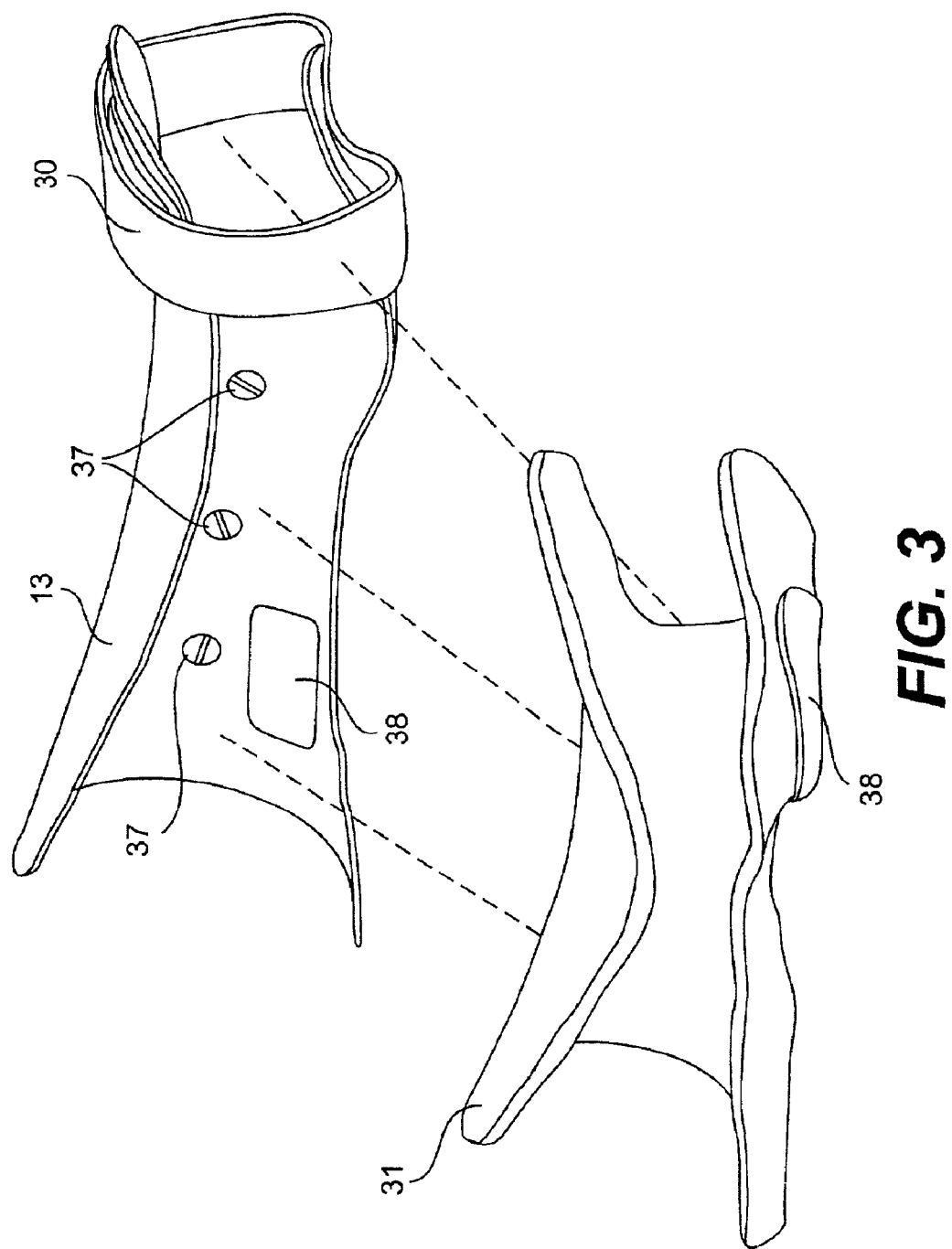
FIG. 3 is an exploded view of the forearm enclosure portion of the orthotic device shown in FIG. 1.
Figure 6:
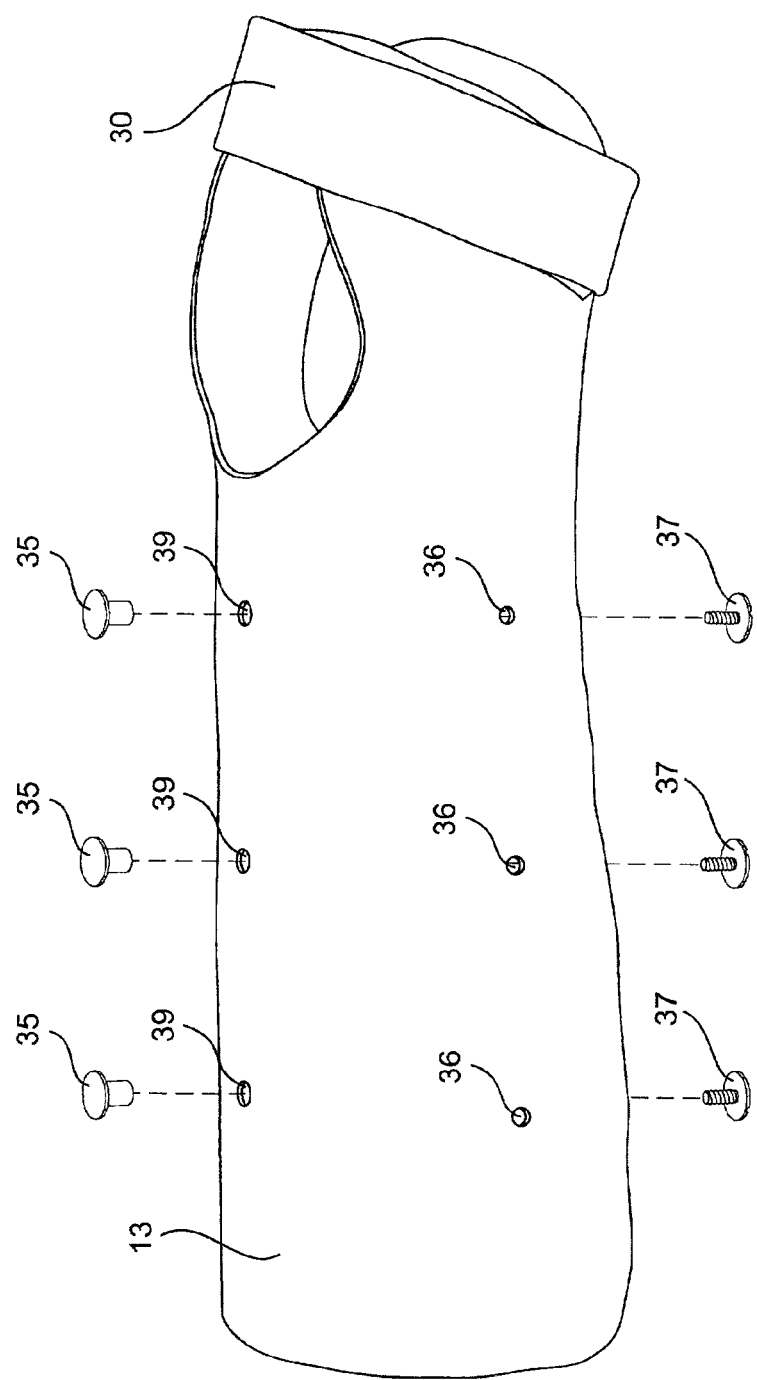
FIG. 6 is a side elevation, partially exploded view of the forearm enclosure portion of a preferred embodiment of the present invention.

Referring now specifically to FIGS. 3 and 6, the forearm enclosure 13 can be more specifically discussed. The forearm enclosure 13 is adapted to engage a patient's forearm and wrist. Strap 30 wraps around the end of the forearm enclosure to secure the end of the forearm enclosure 13 about a patient's hand and wrist. Padding 31 can be used to line the forearm enclosure 13. The padding 31 is connected to the inside of the forearm enclosure 13 by way of patches of hook and loop fasteners 38. The padding 31 is preferably not permanently glued inside the forearm enclosure 13. In this way, the screws 37 that are attached to the posts 35 may be removed and placed in alternative holes 36 or 39 in the forearm enclosure 13. In lieu of the holes 36 and 39 that are predrilled into the forearm enclosure 13, slots (that are not shown) may be used. In this way, the exact position about the perimeter of the forearm enclosure 13 may be selected for the posts 35. Similarly, other types of posts or means of receiving a tensioning member may be used to connect the forearm enclosure to the tensioning member 41.

Figure 5:
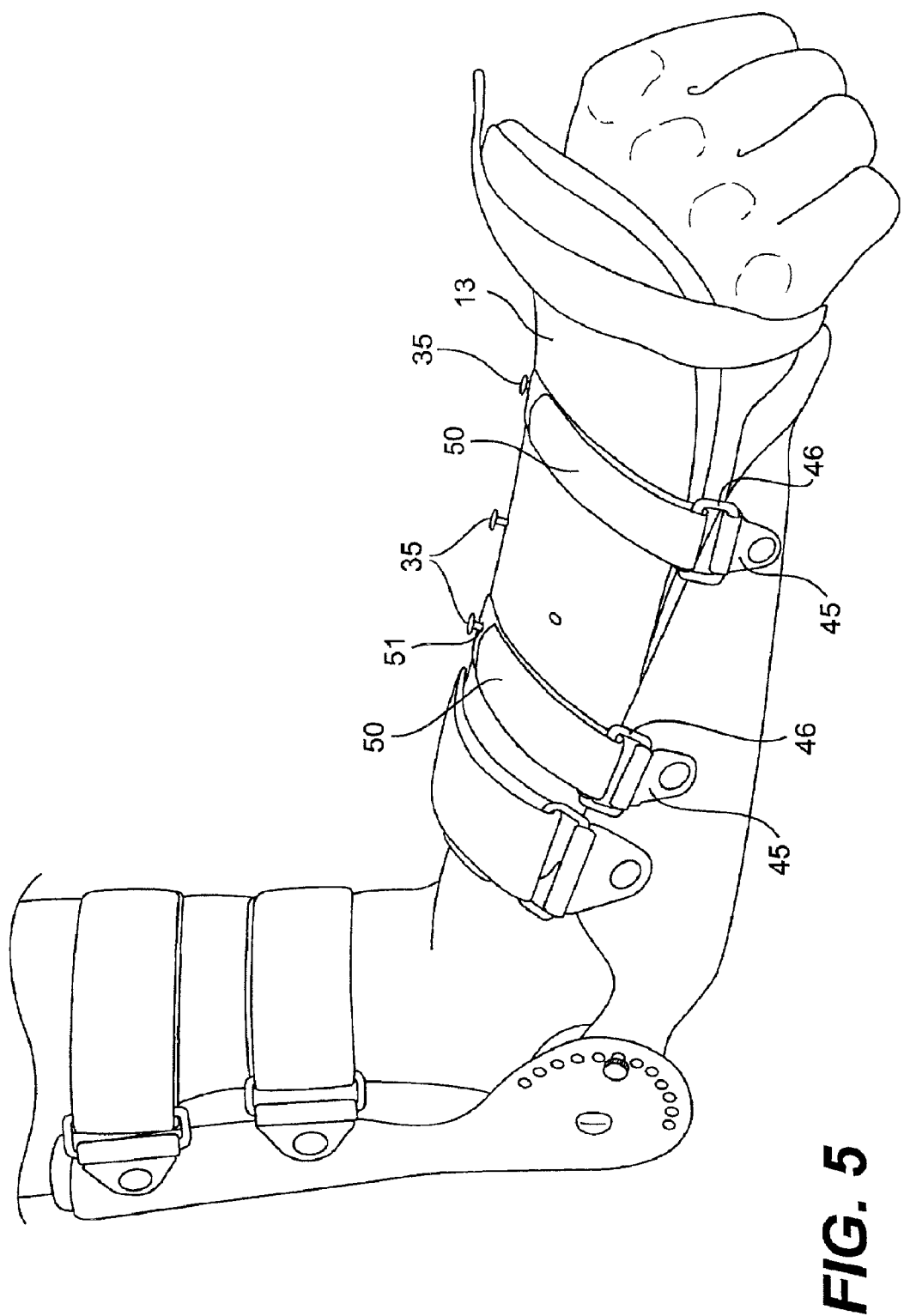
FIG. 5 is an alternative embodiment of an orthotic device in accordance with the present invention.

FIG. 5 illustrates an alternative embodiment of the invention in which a static force of rotation is applied to the forearm enclosure 13. The anchors made up of the bolts 45 and rings 46 are the same anchors as used in connection with the dynamic embodiment described earlier. The tensioning member or straps 50 have a fixed a length that is made of hook and loop fastener (VELCO®) material. The straps 50 are inelastic, and therefore apply no dynamic force on the cast 13. The straps 50 have apertures 51 that loop over the posts 35. The result is that once a strap 50 is attached at one end to a ring 46 and the other end to a post 35, a static rotational force is therefore created on the forearm enclosure 13. These retaining straps 50 may be used alone or together with the dynamic force of the elastic member 41 described earlier.

Many therapeutic scenarios are possible. These include the use of both static and dynamic straps. For instance, a patient could use an elastic member to apply a dynamic force of rotation on a cast for only a part of the day. Other times, the patient could attach the static strap to the wrist in order to maintain a range of motion or to prevent a painful range of motion. Alternatively, both static and dynamic straps could be attached to a post in opposing directions. This could be used to limit rotation in the direction of the dynamic force up to a certain amount. In this way, incremental rotational force is obtained. This also prevents over rotation as a result of a dynamic force. Finally, a patient could use two static straps wrapped around the device in opposite directions in order to set boundaries of rotation of a wrist of a patient. In other words, the static straps would allow a predetermined number of degrees of rotation and could prevent painful or dangerous over rotation by a patient.

The dynamic force of rotation may be adjustable in many different ways in accordance with the present invention. First, the user could change the length of the static straps 40 which are attached to an elastic cord 41. Second, the length of the elastic cord 41 can be varied. Third, the number of posts 35 around which the elastic cord 41 is looped may be varied. Fourth, the elasticity of the cord 41 may be varied. In some therapy, it may be desirable to quantify the treatment. In those cases, a gauge may be used on a post or anchor, or in a strap, to determine the specific amount of rotational force being applied to the cast.

As shown, the device is a brace that is wrapped around both the upper arm and forearm of a patient. This is preferred, because it keeps the forearm support member stable and does not allow it to rotate around a forearm. If the device was a forearm support only, then the support member could rotate around a forearm, thereby removing any rotational force on the wrist (forearm enclosure) of the user. It is preferred that there is at least some support above the elbow that this used to stabilize the forearm support member and not allow the shoulder to accommodate for a lack of rotation.

The device described herein is intended to be simple to use and available to any patient or therapist. Therefore, it is envisioned that a kit containing the components described herein will be available to users or to therapists. Since some of the components will vary in size depending on a given patient, a therapist will be able to easily assemble the parts of the kit to meet individual needs.

While the invention has been described with reference to specific embodiments thereof, it will understood that numerous variations, modifications and additional embodiments are possible, and accordingly, all such variations, modifications, and embodiments are to be regarded as being within the spirit and scope of the invention.

What is claimed is:

1. An orthotic device for promoting supination and pronation comprising:
    a forearm enclosure that substantially wraps around a forearm;
    a forearm support member that wraps partially around the forearm enclosure and that slidably receives the forearm enclosure;
    an upper arm support member connected on one end to the forearm support member and adapted to substantially wrap around and support an upper arm;
    a post mounted on the forearm enclosure;
    an anchor mounted on the forearm support member; and
    a tensioning member connected on one end to the anchor and on the other end to the post, wherein a rotational force of supination or pronation will be created on the forearm enclosure depending on the direction which the tensioning member is extended from the anchor to the post.

2. An orthotic device as described in claim 1, further comprising a plurality of posts mounted at different locations on the forearm enclosure.

3. An orthotic device as described in claim 1, wherein the tensioning member is comprised of an elastic material.

4. An orthotic device as described in claim 1, wherein the tensioning member is comprised of an inelastic material.

5. An orthotic device as described in claim 1, wherein the tensioning member has an adjustable length.

6. An orthotic device as described in claim 1, wherein the upper arm support member is hingedly connected to the forearm support member.

7. An orthotic device as described in claim 1, wherein the upper arm support member is fixedly connected to the forearm support member at a predetermined angle.

8. An orthotic device as described in claim 7, wherein the predetermined angle is substantially 90.

9. An orthotic device as described in claim 6, wherein the angle of connection of the upper arm support member and the forearm support member is variable.

10. An orthotic device for promoting supination and pronation comprising:
    a forearm enclosure that substantially wraps around a forearm;
    a forearm support member that wraps partially around the forearm enclosure and that slidably receives the forearm enclosure;
    an upper arm support member connected on one end to the forearm support member and adapted to substantially wrap around and support an upper arm;
    tensioning means having a first and a second end; and
    means for attaching the tensioning means on the first end to the forearm enclosure and on the second end to the forearm support member,
    wherein a rotational force of supination or pronation will be created on the forearm enclosure depending on the direction which the tensioning means is attached to the forearm support member and the forearm enclosure.

11. A kit far assembling an orthotic device comprising:
    a forearm enclosure that substantially wraps around a forearm;
    a forearm support member that wraps partially around the forearm enclosure and that slidably receives the forearm enclosure;
    an upper arm support member connectable on one end to the forearm support member and adapted to substantially wrap around and support an upper arm;
    a post mountable on the forearm enclosure;
    an anchor mountable on the forearm support member; and
    a tensioning member connectable on one end to the anchor and on the other end to the post.

* * * * *